United States Patent [19]

Manoli

[11] Patent Number: 4,583,549
[45] Date of Patent: Apr. 22, 1986

[54] ECG ELECTRODE PAD

[76] Inventor: Samir Manoli, 4944 Vista Grande, El Paso, Tex. 79922

[21] Appl. No.: 615,247

[22] Filed: May 30, 1984

[51] Int. Cl.⁴ ............................................. A61B 5/04
[52] U.S. Cl. ............................................. 128/640
[58] Field of Search ............................... 128/639–641

[56] References Cited

U.S. PATENT DOCUMENTS

| | | | |
|---|---|---|---|
| 3,380,445 | 4/1968 | Frasier | 128/639 |
| 3,572,322 | 10/1968 | Wade | 128/640 |
| 3,943,918 | 3/1976 | Lewis | 128/640 |
| 3,960,141 | 6/1976 | Bolduc | 128/639 |
| 4,082,086 | 4/1978 | Page et al. | 128/640 |
| 4,233,987 | 11/1980 | Fiengold | 128/639 |
| 4,353,372 | 10/1982 | Ayer | 128/640 |

FOREIGN PATENT DOCUMENTS 2070438   7/1981   United Kingdom ............... 128/641

Primary Examiner—Kyle L. Howell
Assistant Examiner—David Shay
Attorney, Agent, or Firm—Milton D. Wyrick

[57] ABSTRACT

An ECG electrode pad comprising a flexible non-conductive pad with a plurality of ECG electrodes positioned thereon to correspond with the anatomically correct placement for precordial ECG electrodes to be utilized in electrocardiographic monitoring or recording.

4 Claims, 6 Drawing Figures

ECG ELECTRODE PAD

TECHNICAL FIELD

This invention relates to apparatus used to monitor and record the electrical activity produced by the human heart, and more particularly to an arrangement of electrodes useful in electrocardiography (ECG).

BACKGROUND OF THE INVENTION

This invention relates to electrocardiography (ECG) and to electrode arrangements used in electrocardiographic monitoring and recording, and is more particularly related to a pad containing said electrodes and a method for passively and non-invasively monitoring or recording the heart's electrical activity from the surface of a patient's chest, and where desired, correlating such ECG recordings with the standard ECG leads I, II and III.

The electrical potential generated by the heart appears throughout the body and on the surface of the body. Such electrical potentials are helpful to physicians in evaluating the heart's condition. Three basic leads, I, II, and III, make up the frontal plane ECG. These are derived from the various permutations of pairs of electrodes with one electrode located on the right arm, one located on the left arm, and one located on the left leg. When physicians examine the ECG in the transverse plane, they utilize chest leads. In this procedure, electrodes are placed at various anatomically defined positions on the chest wall, and are connected to an ECG recorder. These leads are known as precodial ECG leads. The position of these precordial lead electrodes, designated V1 through V6, is as follows: V1 is located on the fourth intercostal space at the right sternal margin; V2 is located on the fourth intercostal space at the left sternal margin; V3 is located midway between electrode V2 and electrode V4; electrode V4 is located on the fifth intercostal space at the mid-clavicular line; electrode V5 is located on the same level as electrode V4 and on an anterior axillary line; and electrode V6 is located on the same level as electrode V4 and on a mid-axillary line.

Because the surface of the heart is in close proximity to the chest wall, each precordial electrode and its accompanying lead primarily records the electrical activity or potential of the cardiac musculature immediately beneath the electrode position. Therefore, to achieve proper results, the medical technician, particularly when measuring ECG, must be careful to place each chest electrode at its precise location on the chest. When using individual electrodes, this procedure can prove to be inconvenient, time consuming and sometimes inaccurate. Furthermore, if for some reason an precordial ECG recording has to be repeated on the same patient, the probability of locating individual electrodes at the same position is slight. Additionally, the large diameters of convential ECG electrode bodies often results in over lapping of the electrode bodies further complicating proper positioning.

Another use of electrodes is the monitoring of heart activity in intensive care patients who have suffered cardiac problems such as myocardial infarction. In this procedure, three electrodes are placed on the chest of the patient. One is placed in the area of the left shoulder, one in the area of the right shoulder, and one at the end of the sternum.

U.S. Pat. No. 4,328,814 issued May 11, 1982 to Arkens discloses a precordial ECG strip in which individual electrodes are physically connected to one another through bundled conductors terminating in a connector block. Although perhaps more convenient than separate electrodes, this invention also requires the medical technician to individually place each of the six electrodes on the body of the patient, thereby consuming valuable time and making repeatability of measurement subject to inaccuracies because of improper placement. The bundling of conductors in this invention does not materially improve positioning of the electrodes, as each must be individually placed onto the patient's chest. The invention also may be subject to interference and artifact problems because of the close proximity of the bundled conductive leads between electrodes. Further, the plug connector utilized to connect the electrodes with an ECG recorder is not standard within the medical community.

SUMMARY OF THE INVENTION

The purpose of the present invention is to provide an ECG electrode arrangement that is inexpensive, convenient and easy to use by medical personnel, and that allows for a high probability of proper placement of the electrodes on the patient and for easy repeatability of testing. These purposes are accomplished by the placement of the ECG electrodes in their proper relationship to one another on a flexible printed circuit board.

In accordance with the present invention the six ECG electrodes for precordial ECG monitoring or recording, V1 to V6, are prepositioned on a flexible printed circuit board or pad. The prepositioning of electrode V1 to V6 is accomplished to correspond with the proper placement of said electrodes on the body of a patient. Considering the range of sizes of individuals it is envisioned that the great percentage of all patients can be tested by the use of three different pad sizes, namely pediatric, medium size adult and large size adult.

For intensive care monitoring, the three necessary ECG electrodes are similarly positioned in a triangular configuration on a flexible printed circuit board. Their positions correspond with the shoulder and sternum positions necessary for such monitoring.

The present invention comprises a nonconductive flexible printed circuit board having etched on its skin contacting side, at the specific prepositioned locations, thin conductive copper discs. The copper discs are silver plated, and provide the primary skin contact area for ECG and intensive care uses with fewer artifact problems. In the preferred embodiment, connector eyelets are mounted directly above and centered on the silver-plated copper discs to provide releaseable connection with the ECG recorder cables. Silver/silver chloride studs, centered on the silver-plated copper discs constitute the last element of the electrode and provide the electrical connection between the silver-plated copper discs and the connector studs. Thus, the skin contacting surface of the electrode connector is enhanced by the use of both the silver-plated copper discs and the silver/silver chloride eyelets. The connector studs are the standard connectors utilized with ECG recording cables. The silver-plated copper discs and silver/silver chloride eyelets are each covered with a conductive gel and the entire skin contacting surface is coated with a nonconductive adhesive. A release paper covers the entire skin contacting surface to protect the electrodes and the adhesives prior to use.

In another embodiment, the copper discs which are etched on the skin contacting side of the flexible printed circuit board constitute the entire skin contacting surface. In addition to these discs, copper connecting paths from each disc to a connector edge tab, are also etched on the circuit board. The copper discs are again coated with silver, and the copper connecting paths are covered with a non-conductive coating. As in the preferred embodiment, the silver-plated copper discs are coated with a conductive gel, and the rest of the flexible printed circuit board is covered with a nonconductive adhesive and a release paper.

A feature of the present invention is that it allows simple, convenient, accurate, repeatable, passive and non-invasive chest ECG monitoring and recording.

Another feature in the present invention is that it facilitates proper and automatic positioning of ECG electrodes on a patient's chest regardless of that patient's size. Another feature of the invention is that the connecting studs can be connected to any ECG recorder through the standard connectors used on the recorder cables, or through use of a cable with an edge connector.

A further feature is that the invention allows correlative monitoring and recording of the patient's chest and standard ECG leads.

Another feature of the invention is that it can be used with one channel ECG recorders where manual selection of any of the ECG electrodes is necessary.

Another feature of the invention is that it provides a simple, passive and noninvasive technique for accurate recording of a patient's ECG. Yet another feature of the invention is that it can be manufactured inexpensively, allowing it to be disposable; or through the proper cleaning techniques, reused if necessary.

DETAILED DESCRIPTION

Figure 1:
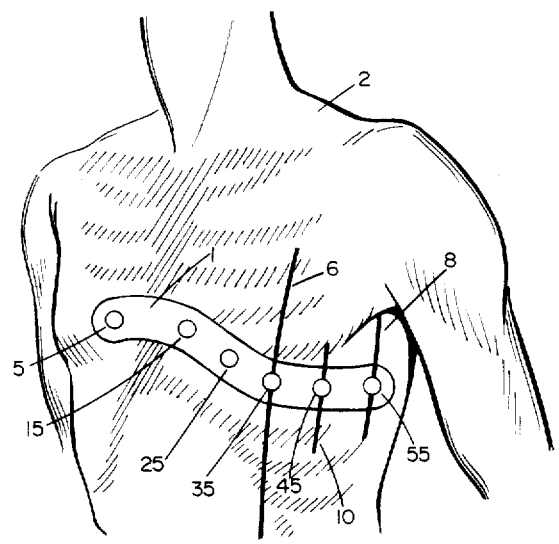
FIG. 1, is a perspective view of a precordial ECG electrode pad of the present invention as attached to a patient and indicating the proper positioning of ECG electrodes V1 through V6.

Referring now to FIG. 1, there is shown a precordial ECG pad 1 placed on the chest of a patient. The V1 ECG electrode 5 is shown in its proper location on the forth intercostal space at the right sternal margin. The V2 ECG electrode 15 is shown at the fourth intercostal space at the left sternal margin. V1 ECG electrode 5 and V2 ECG electrode 15 lie equidistant from the patient's sternum. The V3 ECG electrode 25 is shown midway between V2 ECG electrode 15 and V4 ECG electrode 35. The V4 ECG electrode 35 is located on the fifth intercostal space at the mid-clavicular line 6. The V5 ECG electrode 45 is on the same horizontal level as V4 ECG electrode 35 and on an anterior axillary line 10. The V6 ECG electrode 55 is located also on the same horizontal level as V4 ECG electrode 35 and is on a mid-axillary line 8. FIG. 1 illustrates how the ECG electrode pad 1 is simply placed on the patient 2 by positioning V1 ECG electrode 5 and V2 ECG electrode 15 so that the patient's sternum is equidistant from each, and then pressing the pad into place.

Figure 2:
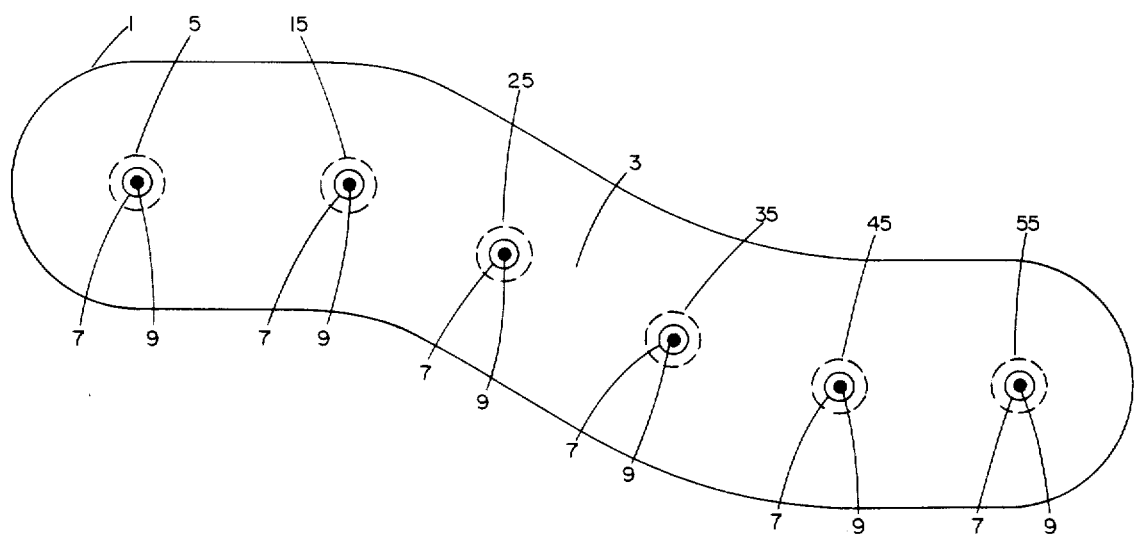
FIG. 2, is an upper plan view of the pad of FIG. 1.
Figure 3:
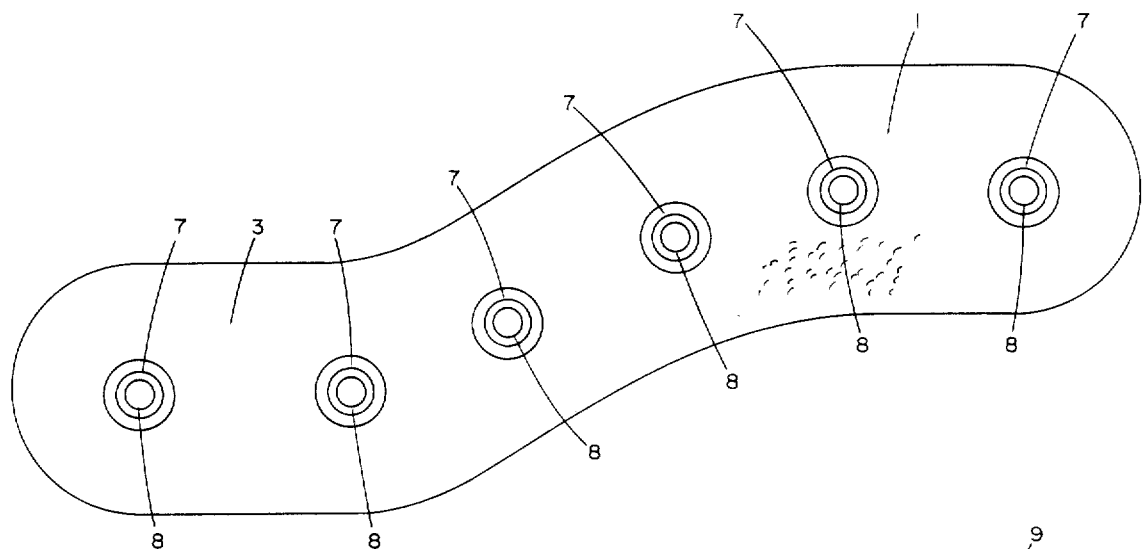
FIG. 3, is a lower plan view of the pad of FIG. 1.
Figure 4:
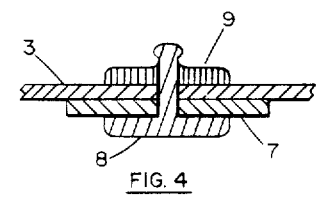
FIG. 4, is a cross-sectional view of one of the ECG electrodes of the pad of FIG. 1.

Referring now to FIGS. 2, 3 and 4, it can be readily observed that the ECG electrode pad 1 consists of a flexible printed circuit board 3, consisting of a non-conductive material such as mylar on which a layer of copper has been placed. The V1 through V6 ECG electrodes, 5, 15, 25, 35, 45, and 55, respectively, are indicated in their proper positions on the flexible printed circuit board 3 to correspond with the anatomically correct placement. The flexible printed circuit board 3 is etched so that copper discs 7 are left on the flexible printed circuit board 3 in the exact position of the V1 through V6 ECG electrodes. The copper discs 7 are plated with silver and have a hole at their centers for receiving the extension of silver/silver chloride electrode studs 8.

The extension of each silver/silver chloride electrode stud 8 extends through the silver-plated copper discs 7 and is pressure fastened into electrical contact within the central portion of connector eyelets 9. Silver/silver chloride electrode studs 8 primarily serve to maintain electrical contact between silver-plated copper discs 7 and connector eyelets 9, although they also constitute a portion of the total skin contact area of the electrodes.

The entire skin contacting side of the electrode pad 3 as shown in FIG. 3, except in the area of the silver-plated copper discs 7 and the silver/silver chloride electrode studs 8, is coated with a pressure sensitive hypo-allergenic adhesive. The silver-plated copper discs 7 and silver/silver chloride electrode studs 8 are each coated with a conductive adhesive gel. This conductive adhesive gel acts as an electrolyte between the contact area of the electrodes and the patient's skin surface. After these adhesives are applied, a protective release paper releasably covers the surface of the ECG electrode pad 3 to protect the electrodes and the adhesives.

Figure 5:
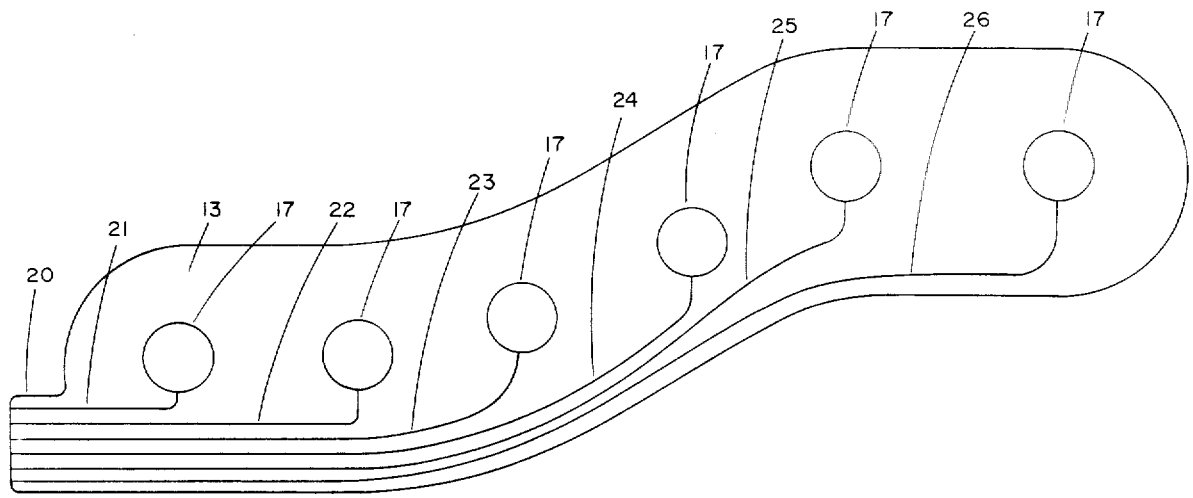
FIG. 5, is a lower plan view of another embodiment of the precordial ECG electrode pad of the present invention.

Referring now to FIG. 5, there is shown another embodiment of the present invention wherein the ECG electrodes, V1 through V6, consist of copper discs 17 which have been produced on the flexible printed circuit board 13 through the etching process in the exact positions of the V1 through V6 electrodes discussed above. Additionally, copper circuits 21, 22, 23, 24, 25 and 26 are also etched on the printed circuit board from each copper disc 17 to a circuit board connector tab 20. In this embodiment a six conductor cable having a six conductor edge connector attached at one end would be used to connect the ECG electrode pad 13 to the ECG recording or monitoring device. The copper circuits 21, 22, 23, 24, 25 and 26 are covered with an insulating coating to avoid contact between the circuits and the patient's skin. This coating is applied prior to the application of the adhesive gel to the silver-plated copper discs 17 and the pressure sensitive hypo-allergenic adhesive to the remaining portions of the skin contacting surface of the electrode pad 13. After these adhesives are applied, a protective release paper releasably covers the skin contacting surface of the flexible printed circuit board 13 to protect the electrodes and the adhesives.

Figure 6:
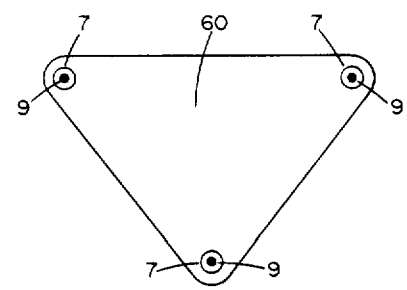
FIG. 6, is an upper plan view of a three ECG electrode pad for intensive care monitoring.

Referring now to FIG. 6, there is shown a triangularly shaped flexible printed circuit board 60 having three of the electrodes illustrated in FIG. 4, with silver-plated copper discs 7 and connector eyelets 9, located at each corner. This is an illustration of the type of pad to be used for monitoring of standard ECG lead II as is often necessary with intensive care patients. This pad would also have conductive adhesive gel over the electrode contact surfaces and the remainder of the pad 60 would be covered with a pressure sensitive hypo-allergenic adhesive. This pad would also be covered by release paper to protect the electrodes and adhesives prior to use.

To use any of the embodiments shown in FIGS. 1 through 6, the medical personnel conducting the ECG monitoring or recording simply remove the release paper from the skin contacting side of the ECG electrode pad to expose the pressure sensitive adhesive and the conductive adhesive gels. In the case of the six electrode ECG pads the V1 and V2 ECG electrodes are simply placed on the patient's chest on each side of the sternum, and the remainder of the pad is then pressed onto the patient's chest. This results in the precordial ECG electrodes being positioned in their precise anatomical locations. In the case of the ECG electrode pad of FIG. 6, the triangular shaped pad is placed so that two of the electrodes lie on the patient's right and left upper chest area with the third electrode falling in the midsection of the chest. After application of any of these ECG electrode pads to the patient's body, leads are connected to the ECG pad either by individual snap connectors or through an edge connector and cable to connect the electrodes from the ECG electrode pad to the recording or monitoring means.

Thus, in accordance with the present invention, the ECG electrode pad may be applied to the patient with its prepositioned electrodes in a simplified and convenient manner. In addition, the snap connectors on the ECG recording or monitoring cable may be snapped onto the snap connectors of the ECG electrode pad or the edge connector of the cable may be connected to the ECG electrode pad in a simplified manner.

Obviously, many modifications and variations of the present invention are possible when considered in the light of the above teachings. It is therefore understood that the full scope of the present invention is not limited to the details disclosed herein and may be practiced otherwise than is specifically described.

What is claimed is:

1. A precordial ECG electrode pad comprising:
   (a) a flexible nonconductive body having a fixed precordial configuration;
   (b) six conductive discs plated on said flexible nonconductive body and etched to a predetermined pattern effective for precordial ECG disc placement, two of said six discs having fixed locations for equidistant placement on opposite sides of a patient's sternum;
   (c) the four remaining ECG discs fixedly positioned on said flexible nonconductive body at predetermined locations relative to said two discs for anatomically correct placement for sensing precordial ECG signals from said patient's body at locations corresponding to a first location at a fifth intercostal space along the mid-clavicular line, to a second location about mid-way between said first location and an adjacent one of said two discs, to a third location on an anterior axillary line; and to a fourth location on a mid-axillary line, said first, third, and fourth locations generally defining a horizontal plane; and
   (d) conductor means on said nonconductive body for separately connecting each of said discs to ECG recording or monitoring means.

2. The ECG electrode pad of claim 1 wherein the lower side of said flexible nonconductive body is coated with a hypoallergenic pressure sensitive adhesive coating.

3. The ECG electrode pad of claim 2 wherein said six ECG electrodes are each coated with a conductive adhesive gel coating.

4. The ECG Pad of claim 3 wherein the entire lower side is covered with a removable release paper.

* * * * *